(12) United States Patent
Heanue et al.

(10) Patent No.: US 8,269,964 B2
(45) Date of Patent: Sep. 18, 2012

(54) PHOTON MEASUREMENT METHOD AND APPARATUS

(75) Inventors: John F. Heanue, San Jose, CA (US);
Joseph A. Heanue, Palo Alto, CA (US);
Brian P. Wilfley, Los Altos, CA (US);
Augustus P. Lowell, Durham, NH (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1143 days.

(21) Appl. No.: 11/381,450

(22) Filed: May 3, 2006

(65) Prior Publication Data
US 2007/0260145 A1 Nov. 8, 2007

(51) Int. Cl.
*G01J 3/30* (2006.01)
(52) U.S. Cl. ......... 356/317; 356/5.1; 356/336; 356/445; 356/446; 600/407; 600/476
(58) Field of Classification Search .......... 600/407, 600/476; 356/336, 5.1, 445, 446, 317; 60/407, 60/476
See application file for complete search history.

(56) References Cited

U.S. PATENT DOCUMENTS

| 5,000,568 | A | * | 3/1991 | Trutna et al. | 356/73.1 |
| 5,447,159 | A | * | 9/1995 | Schultz | 600/477 |
| 5,460,182 | A | * | 10/1995 | Goodman et al. | 600/342 |
| 5,565,982 | A | | 10/1996 | Lee et al. | |

OTHER PUBLICATIONS

Gibson et al., "Recent Advances in Diffusion Optical Imaging," Phys. Med. Biology, vol. 50, R1-R43 (2005).
DeGrand et al., "An Opereational Near-Infrared Fluorescence Imaging System Prototype for Large Animal Surgery," Technology in Cancer Research and Treatment, vol. 2, No. 6, pp. 1-10 (2003).
Chen et al., "Time-resolved Optical Measurements with Spread Spectrum Excitation," Optical Letters, vol. 27, No. 20, pp. 1806-1808 (Oct. 15, 2002).
Hielscher et al., "Near-infrared Diffuse Optical Tomography," Disease Markers, vol. 18, 313-337 (2002).

* cited by examiner

*Primary Examiner* — Tse Chen
*Assistant Examiner* — Jason Ip (57) ABSTRACT

A system and method for measuring photons utilizing a low-power light source modulated with a code sequence to interrogate a sample of interest. Preferably a portion of the scattered light from the sample is detected by a photo-detector. A correlation of the photo-detector signal and the code sequence produces an estimate of the distribution of flight times for photons traveling from the source to the detector.

5 Claims, 7 Drawing Sheets

PHOTON MEASUREMENT METHOD AND APPARATUS

FIELD OF THE INVENTION

The field of the present invention pertains generally to systems and methods for detecting and measuring photons, including, more specifically, the measurement of the time-of-flight of photons traveling through a scattering media such as tissue.

BACKGROUND

Diffuse optical imaging techniques are known in medical and biological applications. Overviews of diffuse optical imaging techniques can be found in "Recent Advances in Diffusion Optical Imaging" by Gibson, et al, Phys. Med. Biology, vol. 50 (2005), R1-R43and in "Near-infrared Diffuse Optical Tomography," by Hielscher, et al, Disease Markers, Vol. 18 (2002), 313-337. Briefly, diffuse optical imaging involves the use of near-infrared light incident upon a sample of interest. An example in the medical and biological field is optical mammography where near infrared light is used to illuminate breast tissue. A detector is placed on the opposite side of the breast from the incident light some distance away and collects scattered light from the breast tissue. The scattered light of interest that is detected may be directly scattered incident light or scattered fluorescence light caused by the excitation of an injected fluorescing material that fluoresces when exposed to the incident light. By measuring the amplitude of the light of interest at the detector and the distribution of photon arrival times at the detector for various source and detector positions, a reconstruction of the underlying tissue optical properties can be made. An overview of image reconstruction techniques can be found in the citations given in the aforementioned review articles.

Measurements of the photon flight-time distributions are typically carried out using either the time-domain or the frequency-domain technique. In the time-domain technique, the sample is excited with a pulse of light from a pulsed laser and the scattered light is measured using a detector with single-photon sensitivity. The detector measures the time delay between the excitation pulse and the first detected photon. The flight-time distribution is determined by using many repeated pulses and building up a histogram of the measured time delays. Unfortunately, the pulsed laser sources and single-photon detectors are relatively expensive. Because detection is typically done at the single-photon level, it can require a significant amount of time to build-up enough data to approximate the flight-time distribution. One disadvantage of the frequency-domain approach is that it is not a direct measurement of the photon flight time. Rather, it provides an estimate of the mean flight time based on the phase shift between a detected signal and the excitation signal. In some cases, more accurate image reconstructions can be obtained using more complete measurements of the flight-time distributions. This data is not readily obtained with frequency-domain instrumentation. A further disadvantage of the frequency-domain approach is the need for accurate high-frequency analog electronics. An overview of both the time-domain and frequency-domain techniques can be found in the above-referenced article by Hielscher, et al.

U.S. Pat. No. 5,565,982 discloses a time-resolved spectroscopy system using digital processing techniques and two low power, continuous wave light sources. The disclosed system requires two light transmitters of different wavelengths modulated with separate codes for interrogating a sample of interest. Properties of the sample are inferred by differential comparison of the return signals from each of the two light sources. It is undesirable to have two distinct light sources due to the cost and complexity involved. Furthermore, the noise level associated with a measurement made with two separate light sources will be higher than with a single source even if the codes used to drive the two sources are orthogonal.

A system and method capable of addressing these disadvantages while providing acceptable temporal information for whatever application the photon measurement is being used is needed.

SUMMARY OF THE INVENTIONS

The inventions presented herein provide for direct measurements of photon flight-time using any single light source modulated with a known digital pattern. A preferred system uses information from a single low-power continuous-wave light source detected by a low-cost detector. Preferably the measurement system is implemented with digital electronics. One embodiment of the system and methods disclosed comprises an information from a single continuous-wave light source modulated with a digital waveform for interrogating a sample, a photo-sensitive detector for measuring the scattered light from the sample, and electronics for sampling the detector output and performing a correlation of the output signal with the modulation waveform. Other embodiments include electronics and software for determining the parameters of the flight-time distribution from the measured correlation.

DETAILED DESCRIPTION OF THE DRAWINGS

Figure 1:
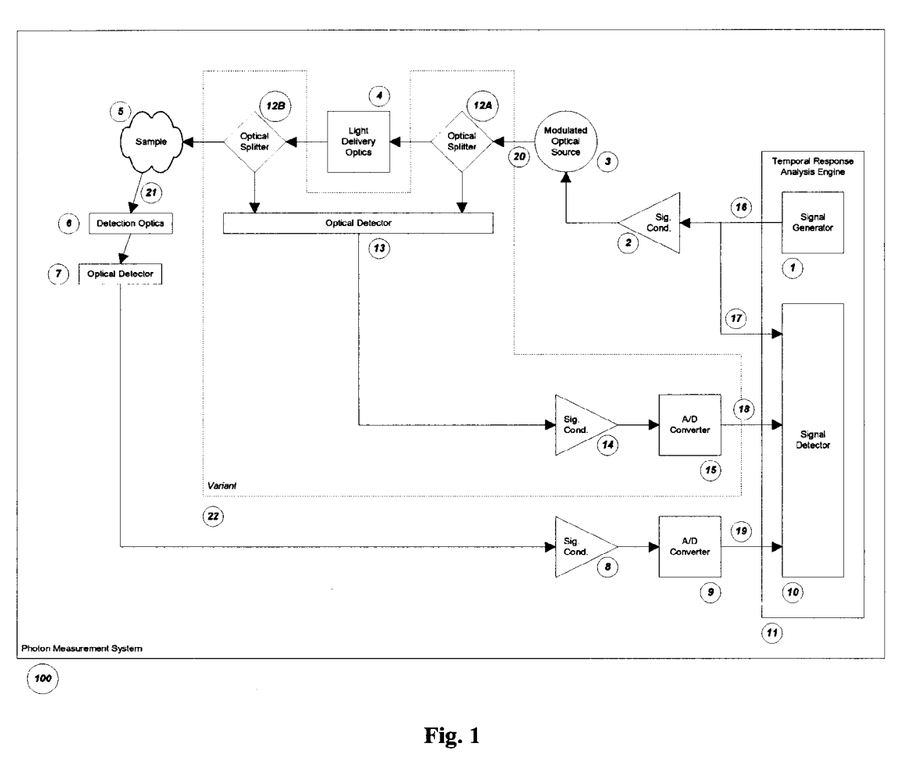
FIG. 1 is a functional block diagram of the major components of a preferred photon measurement system of the present invention.

A functional block diagram of a preferred photon measurement system 100 is depicted in FIG. 1. The photon measurement system can be used to measure the interaction of photons with a sample 5. In certain applications, the sample 5 may be human breast tissue or fat tissue but it could just as well be any semitransparent material. The photon measurement system 100 preferably includes Temporal Response Analysis Engine 11. The Temporal Response Analysis Engine 11 generates a digital modulation signal for driving an illumination light source that is used to interrogate the sample. The Temporal Response Engine 11 also provides a means for processing a detected optical signal from the sample 5 to extract information about the sample 5. Preferably a digital modulation signal 16 is generated in the signal generator 1 and transmitted to the transmit signal conditioner 2. The digital modulation signal 16 is the digital representation of a chosen code sequence. The code sequence is preferably chosen from the known pseudorandom binary sequences (PRBS), Gold codes, Golay codes, Kasami codes, Walsh codes, or other codes that possess the preferred desirable property of large auto-correlation values and low cross-correlation values. The digital modulation signal 16 may represent a single code pattern or multiple repeats of the same pattern. A single complete set of code patterns is designated a modulation frame or code pattern frame. The digital modulation signal 16 is preferably transmitted to the signal detector 10 as an electronic reference signal 17. The transmit signal conditioner 2 formats the digital modulation signal 16 as necessary to drive an optical illumination source 3. In the preferred photon measurement system 100, the optical illumination source is a 785 nm continuous wave diode laser made by Hitachi Corp. Formatting of the digital modulation signal 16 in the preferred embodiment involves converting the digital modulation signal 16 to an analog voltage waveform that is coupled through a 50-ohm bias-T to the DC drive current of the optical illumination source 3. In other embodiments, the optical illumination source 3 may be a different laser diode, a light-emitting diode, or a light source used together with an external optical modulator. The optical illumination source 3 generates the modulated optical wave 20 which is preferably transmitted to the sample 5 by light delivery optics 4. The preferred light delivery optics 4 is a 3 mm diameter fiber bundle located between the optical illumination source 3 and the sample 5 to deliver the modulated optical wave 20 from the optical illumination source 3 to the sample 5. In other embodiments the light delivery optics 4 comprises other arrangements of optical fibers, lenses, mirrors or other optical delivery components. When the modulated optical wave 20 illuminates the sample 5, scattered optical waves 21 are generated. In the preferred photon measurement system, the sample 5 is treated with a fluorescent material that will fluoresce when it is illuminated by the modulated optical waves 20. In the preferred system the scattered optical waves 21 are fluorescence generated from a fluorescent material within the sample 5. The fluorescent material is preferably an exogenous contrast agent injected into the sample 5 or alternatively it is preferably some constituent component of a material that exhibits endogenous fluorescence. The detection optics 6 are situated so that a portion of the modulated optical waves 21 are detected by the detection optics 6. In the preferred photon measurement system 100, the detection optics 6 include an optical filter for separating the fluorescing scattered optical waves 21 from the modulated optical waves 20. The optical filter preferably transmits the higher wavelength fluorescence and blocks the lower wavelength illumination light. In applications where the scattered optical waves 21 of interest are not fluorescing, an optical filter is not required.

In the preferred photon measurement system 100, the detection optics 6 preferably include a second 3 mm diameter fiber bundle located between the optical filter and the optical detector 7. The optical detector 7 converts the scattered optical waves 21 to an electronic signal. In the preferred photon measurement system 100, the optical detector 7 is preferably a photomultiplier tube, model R7400U-20 from Hamamatsu Corp. In other embodiments, the optical detector 7 may be a PIN photodiode, an avalanche photodiode, a charge-couple device, or other suitable photosensitive element. As previously stated, the optical detector 7 preferably converts detected scattered optical waves 21 into an electronic signal which is communicated to the detected signal conditioner 8. The detected signal conditioner 8 preferably formats the signal so it may be converted to discrete samples by an Analog to Digital (A/D) converter 9. The A/D converter 9 outputs a detected response signal 19. The detected response signal 19 is communicated to a signal detector 10, where it is preferably correlated with the electronic reference signal 17 to extract a sample transfer characteristic.

Information about the temporal properties of the photons is preferably calculated from the sample transfer characteristic. This information preferably includes such properties as direct measurements of photon time-of-flight and the fluorescence lifetime. The estimate of photon times-of-flight is then preferably used to estimate characteristics of the tissue such as the absorption coefficient, scattering coefficient, or location of fluorescing material.

Another embodiment of the photon measurement system 100 includes an optical reference generator 22. The optical reference generator 22 preferably includes an optical splitter 12A or 12B that routes a portion of the modulated optical wave 20 to a secondary optical detector 13. The position of the optical splitter 12A or 12B can be either before or after the light delivery optics. The output of the secondary optical detector 13 is preferably routed to a secondary signal conditioner 14 whose output is communicated to a secondary A/D converter 15. The secondary A/D converter 15 preferably outputs a source reference signal 18 which can be correlated with the detected response 19 to extract the sample transfer characteristic. Using the source reference signal 18 as opposed to the electronic reference signal 17 allows the filtering of the temporal properties of the signal conditioner 2 and the modulated optical source 3 from the measured transfer characteristic.

Figure 2:
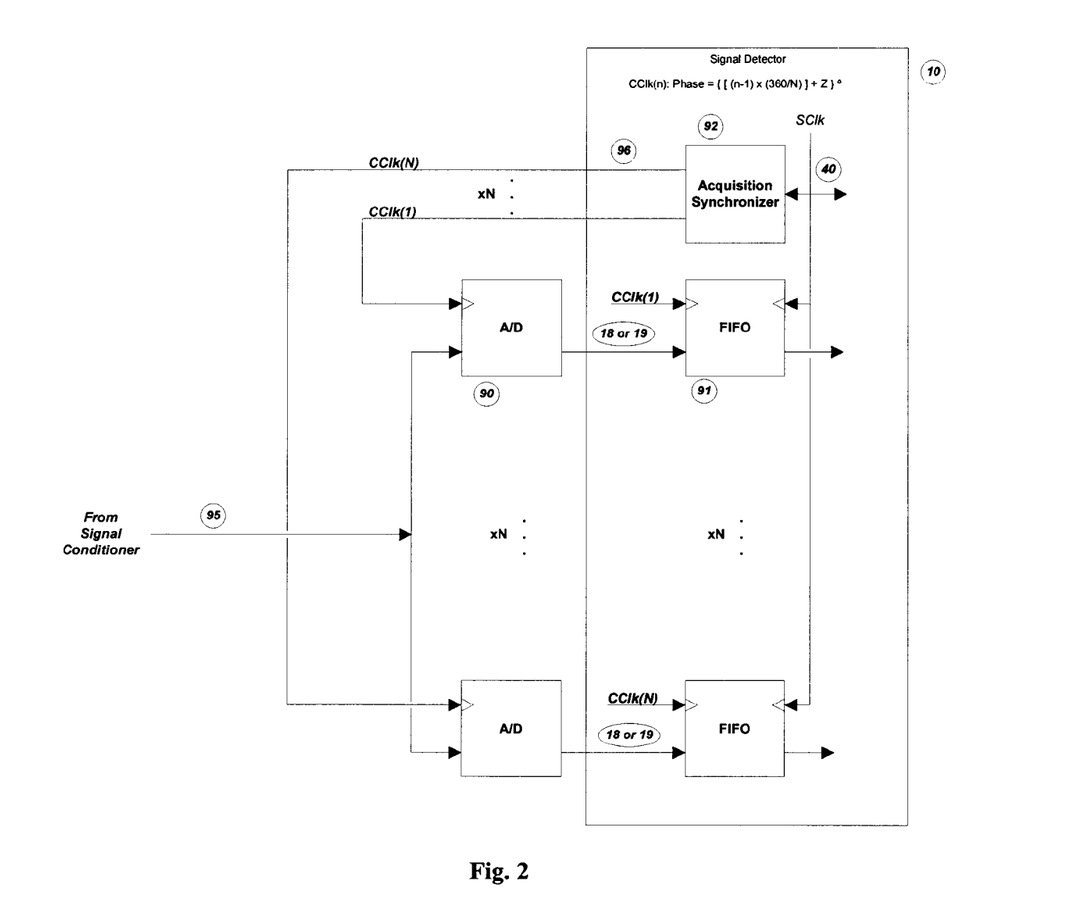
FIG. 2 is a diagram of preferred Analog-to-Digital converters and their interface to the signal detector.

The preferred hardware implementation of the A/D converter module and its interfaces to the signal detector 10 are shown in FIG. 2. An array of N A/D converters 90 preferably receives the analog signal 95 in parallel from the signal conditioner 8 or 14. The output samples 18 or 19 from the A/D converters 90 are preferably communicated to the First-In-First-Out buffers (FIFOs) 91 where they are buffered for distribution to the internal components of the signal detector 10. In the preferred photon measurement system the A/D converters 90 are eight MAX 108 integrated circuits made by Maxim operating at 250 Msample/sec and outputting two data samples at a time in parallel at 125 MHz. The FIFOs 91 are preferably implemented within a Xilinx 4 FPGA. The acquisition synchronizer 92 preferably controls signal acquisition and digital data distribution through the conversion clock (CClk) signals 96.

The acquisition synchronizer 92 is preferably synchronized with an externally provided synchronization clock (SClk) 40 which is also preferably used to synchronize the signal generator 1. The signals CClk[1 . . . N] are preferably generated within the acquisition synchronizer 92 and preferably have the same frequency as SClk 40 but are offset in phase from SClk 40 in N fixed increments of $(360 \div N)°$, with the phase of CClk[1] set to the fixed offset of Z°. In the preferred system the internal clock generation capabilities of the Xilinx FPGA are used to implement the acquisition synchronizer 92 directly. The A/D converters 90 preferably perform their conversions in sync with the conversion clocks 96 such that they generate samples at N discrete sample times spread evenly throughout the fundamental sample interval defined by the period of SClk 40. The effective sample rate for the array of converters is preferably N times the rate defined by SClk 40. This process of using multiple A/D converters sampling out of phase to increase the effective sample rate is what we call parallel over-sampling. In the preferred photon measuring system, parallel over-sampling results in an effective sample rate of 2 Gsamples/sec. The offset value Z allows the entire sample set to be offset by some phase from the synchronization clock 40. The acquisition synchronizer 92 preferably is configured such that the value of Z can be varied synchronously with the modulation frame, or with a block of frames called a frame block. This allows Z to follow a sequence of K values smaller than $(360 \div N)°$ such that on successive modulation frames/frame blocks the effective sampling phases (relative to the synchronization clock) take on K values intermediate to those created by the N conversion clocks in any given frame. In this case preferably the input signal at any given A/D converter 90 will be sampled at K discrete phases over K blocks. The detected response 19 is preferably assumed to be stationary with respect to the start of the code pattern block over that time interval. The preferred K discrete sampling phases correspond to K discrete sample times and the effective temporal resolution of the sampling process is preferably increased by a factor of K. This process is referred to as temporal over-sampling.

In the preferred photon measuring system the value of Z is always zero and temporal over-sampling is achieved by adjusting the phase of the modulation as described below rather than by adjusting the phase of the A/D converter sampling. Preferably the FIFOs latch input data to the A/D converters 90 synchronously with the corresponding conversion clock 96. The FIFO 91 output data is preferably provided to the internal components of the signal detector 10 synchronously with the synchronization clock 40 such that all further processing is synchronized with the synchronization clock 40.

Figure 3:
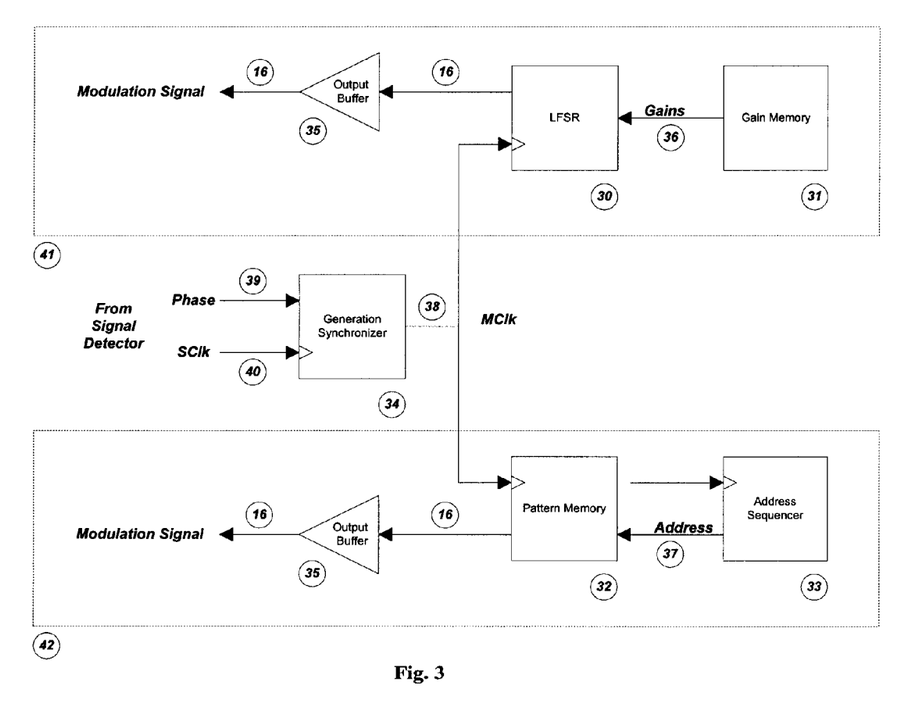
FIG. 3 is a functional block diagram of a preferred signal generator.
Figure 4:
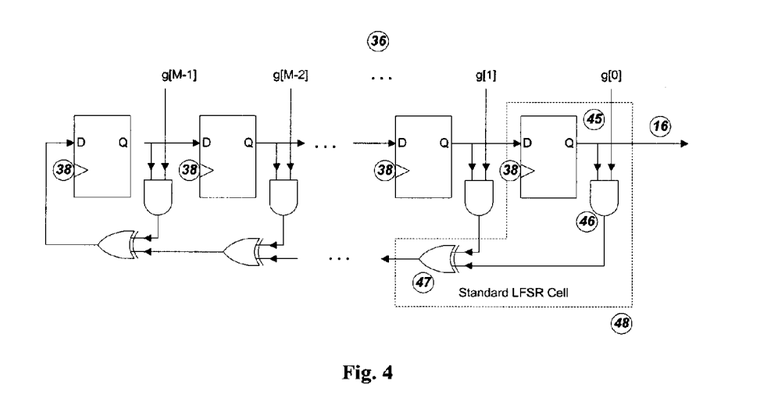
FIG. 4 depicts an implementation of a preferred Linear Feedback Shift Register.
Figure 5:
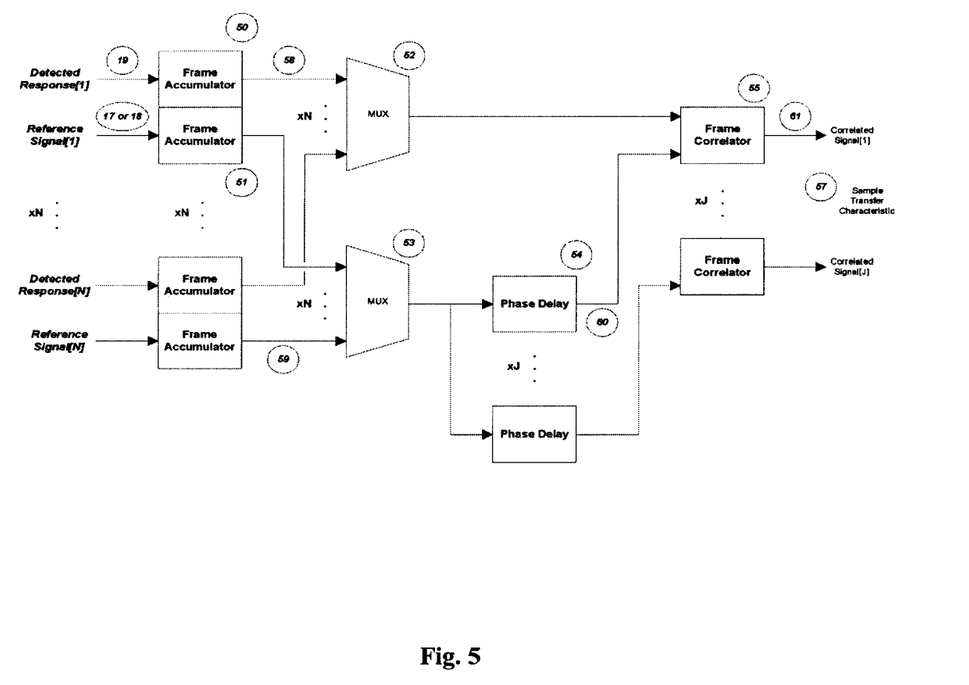
FIG. 5 is a functional block diagram of a preferred signal detector.
Figure 6:
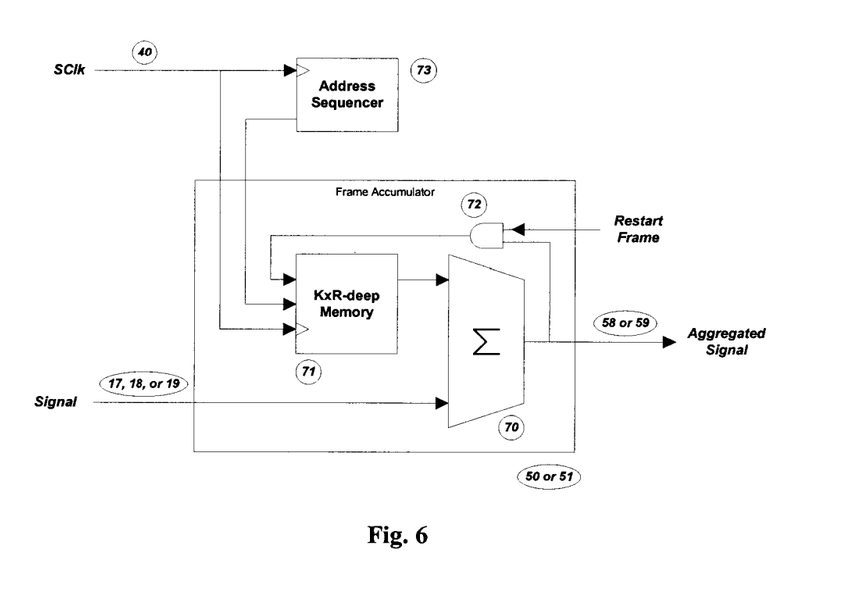
FIG. 6 is a functional block diagram of a preferred frame accumulator.
Figure 7:
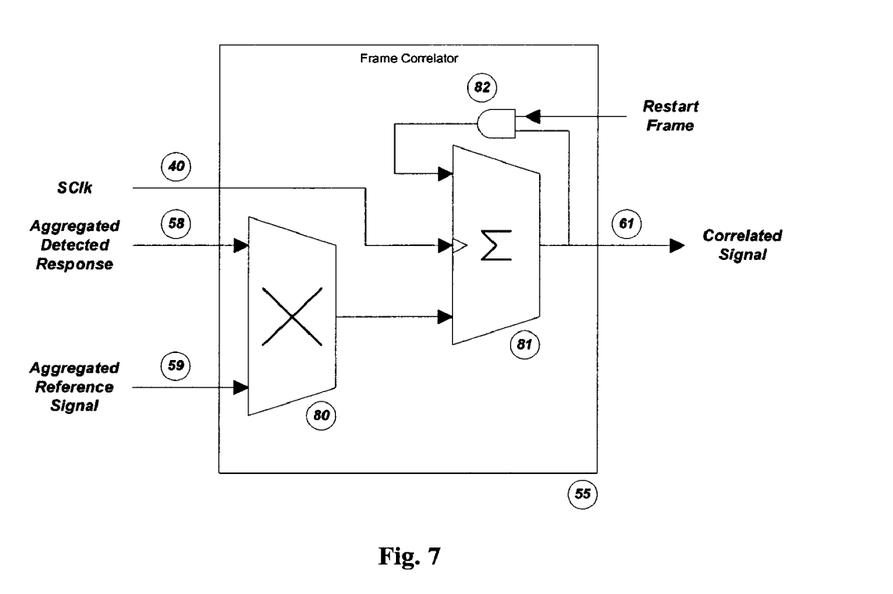
FIG. 7 is a functional block diagram of a preferred frame correlator.

The preferred implementation of the Temporal Response Analysis Engine 11 are shown in FIGS. 3 through 7; the preferred signal generator 1 is shown in FIGS. 3 and 4, while the preferred signal detector 10 is shown in FIGS. 5, 6, and 7. In the preferred system the Temporal Response Analysis Engine 11 is implemented as logic blocks within a Xilinx 4 FPGA.

The functional blocks of the preferred signal generator 1 are shown in FIG. 3. The top 41 and bottom 42 signal paths are two preferred variants for generating different code patterns for the modulation signal 16. In the top path 41 a Linear Feedback Shift Register (LFSR) 30 is preferably used to create a PRBS code. The specific code pattern is preferably determined by the number of state bits within the LFSR 30 and the gain code 36 input to the LFSR 30. In one preferred implementation the gain code 36 is stored in a gain memory 31, which is preferably configured to allow the code pattern 16 to be changed during operation either by selecting one of several gain codes from a read-only memory or by setting a new gain code into a writable memory. In other embodiments the gain code 36 may be hard-wired into the LFSR 30, or a code-specific state-machine designed to generate a desired code through a series of state transformations may be used in place of the LFSR 30. In the bottom path 42 the entire code pattern is preferably stored as a bit sequence in a pattern memory 32. The sequence in which pattern bits are presented is preferably determined by an address sequencer 33 which preferably provides the cell addresses 37 for the memory. The address sequencer 33 is preferably configured to allow changing the code pattern 16 during operation either by selecting one of several patterns stored in a read-only memory or by inputting a new pattern into a writable memory.

The modulation signal 16 for both the LFSR 30 or pattern memory implementation is preferably buffered by an output buffer 35 to make the signals 16 more robust when driving external components. Timing for presentation of the code pattern bits is preferably controlled by a generation synchronizer 34 which preferably generates the master clock (MClk) 38 for the LFSR 30 and the address sequencer 33. The master clock 38 is preferably synchronized to a system synchronization clock (SClk) 40 which preferably controls both code pattern generation and response signal acquisition. MClk 38 preferably operates at the same frequency as SClk 40 but is preferably offset in phase by an amount specified by the phase input 39, which is preferably an externally programmable parameter. This phase offset allows the relative phase between the modulation signal 16 and the detected response 19 to be adjusted. If the phase is adjusted by some increment, $(360 \div K)°$, at the end of each code pattern block or set of blocks the detected response resulting from the modulation signal will preferably be sampled at K discrete phases over K blocks. In this embodiment of the photon measuring system as with the preferred embodiment, the detected response 19 is assumed to be stationary with respect to the start of the code pattern block over that time interval so that the K discrete sampling phases correspond to K discrete sample times and the effective temporal resolution of the sampling process is increased by a factor of K.

This temporal over-sampling is functionally equivalent to the technique described for temporal over-sampling in the A/D converter embodiment. In other embodiments the external phase specification may represent the phase increment rather than the absolute phase, and the generation synchronizer 34 may increment the phase internally.

The preferred implementation of the LFSR 30 is shown in FIG. 4. The LFSR 30 is preferably a state-machine comprising M standard LFSR cells 48 which hold and transform the state. The LFSR cells 48 are preferably linked in a numbered sequence, and the output from the LFSR 30 is the current state of cell number zero. Each cell preferably comprises a state latch 45 which holds a single bit of state information, a gain element 46 to control the feedback gain for the cell based on the externally provided gain code 36, and an accumulator 47. The accumulator 47 preferably adds the feedback from the cell to the cumulative feedback from all previous cells. At each clock increment the state for a cell is updated to match the previous state from the next higher cell in the chain; the state of the last cell in the chain is updated with the accumulated feedback from all the previous cells. The accumulator 47 for the last cell in the chain may be omitted if desired. The pattern generated by the LFSR 30 is preferably determined by the number of cells in the chain and by the gain code. In a preferred embodiment the gain code is provided from an external source to allow the code pattern to be modified. In other embodiments the gain code may be a fixed value. In embodiments in which the gain code is fixed, the implementation of the gain elements and accumulators for each cell may be optimized for the specific gain code for that cell rather than implemented in the generalized fashion shown. The clock for the LFSR 30 and for all its internal latches is preferably the signal generator master clock 38.

The preferred functional blocks for the signal detector 10 are shown in FIG. 5. The detected response 19 and either the electronic reference signal 17 or the source reference signal 18 are received at two frame accumulators 50 and 51, where the samples for each discrete sample time are accumulated with samples from identical sample times from different modulation frames to form the aggregated detected response 58 and the aggregated reference signal 59. As a result of this aggregation, the effective data rate at which samples are preferably processed in following blocks is reduced by a factor equal to the number of frames aggregated into each sample point. The frame accumulators 50 and 51 are preferably replicated N times to handle the N channels of the A/D converter independently. The internal details of the frame accumulators 50 and 51 for the detected response and the reference signal may differ, depending on the digital format of the two signals. For example, if the reference signal used for analysis is the electronic reference signal 17 rather than the source reference signal 18 its value for each sample time is known a priori to be identical for every frame and to take on only two possible binary values, 0 or 1. In that case preferably the frame accumulator 51 for the reference signal 17 need only store one bit per sample time, equal to the value of the modulation signal for that sample time. At some point between the output of the frame accumulators and final output of the sample transfer characteristic 57 the N acquisition/accumulation channels are preferably re-interleaved into a single data stream. In one preferred embodiment two multiplexers 52 and 53 perform this reintegration at the output of the frame accumulators 50 and 51. In other embodiments this re-integration may take place at any other desired point in the signal processing chain. With or without re-integration the aggregated detected response 58 and the aggregated reference signal 59 are routed to the frame correlator 55 where the two signals 58 and 59 are preferably combined by a cross-correlation algorithm to produce the correlated signal 61 which preferably comprises a single value for each complete aggregated frame of samples. The correlated signal 61 represents the degree to which the aggregated response signal 58 contains components matching the aggregated reference signal 59. If the aggregated reference signal 59 is delayed by a time τ before presentation to the correlator 55 then the correlated signal 61 represents the degree to which the aggregated response signal 58 contains components of the delayed version of the aggregated reference signal 60. The sample transfer characteristic 57 comprises a set of correlated signals calculated for a range of J such delay times. Phase delay blocks 54 generate the delayed versions of the aggregated reference signal 60. For simplicity the J phase delay blocks 54 are illustrated as discrete components operating in parallel and each providing the complete delay required for one correlated signal. In one preferred embodiment they comprise a cascade of J phase delay blocks each providing the time increment between one correlated signal and the next. The phase delays for the correlated signals are preferably discrete and correspond to integral multiples of the synchronization clock 40 period. The phase delay blocks 54 are preferably implemented as shift registers or FIFOs of the appropriate depth and clocked by the synchronization clock 40. In other embodiments the time delay may be implemented using other methods. In one preferred embodiment each phase delay is processed by a corresponding frame correlator 55. In other embodiments a single frame correlator 55 may be used to calculate the correlated signal 61 for multiple phase delays by presenting the detected response data to its input multiple times, using a different phase delayed version of the reference signal 60 for each iteration. In this case fewer frame correlators 55 are required.

The details of the preferred frame accumulator 50 or 51 are shown in FIG. 6. Samples from the signal 17, 18, or 19 are preferably accumulated in the adder 70 by summing them with values taken from the memory 71; the resulting aggregated signal 58 or 59 is routed to the output of the accumulator and stored back into the memory at the same location from which the original data was taken. Each discrete sample time for the channel is represented by a single addressed cell within the memory. The size of the memory is preferably determined by two parameters, K and R, which preferably encode the sampling scheme. K represents the number of discrete phases at which samples are preferably taken in various frames during temporal over-sampling. R is the ratio of the number of samples in a modulation frame to the number of sampling channels provided in the A/D converter 90 for parallel over-sampling and signifies the number of samples that must be accommodated by each channel within a single frame. A preferred sample enable gate 72 is provided to restart the accumulation process at the beginning of each set of frames by clearing the cells in the memory. The address sequencer 73 selects the cell of the memory to be addressed for each sample point. The frame accumulators 50 or 51 preferably run synchronously with the synchronization clock 40 (although out of phase), so only a single address sequencer is required to address all the frame accumulators.

The details of the preferred frame correlator 55 are shown in FIG. 7. The ideal method for correlating the signals is to take the integral of the detected response 19 weighted by the reference signal 17 or 18. Because the preferred embodiment is a sampled system the integration is approximated by summation over all the samples within a frame set using the adder 81 to generate the correlation signal 61. The weighting of the aggregated detected response 58 by the aggregated reference signal 59 is preferably performed by a multiplier 80. Other embodiments may employ other weighting and integration schemes, including scaling and integration in the analog domain directly on the detected signals. A sample enable gate 82 is preferably provided to restart the accumulation process at the beginning of each set of frames by clearing the correlator.

Figure 8:
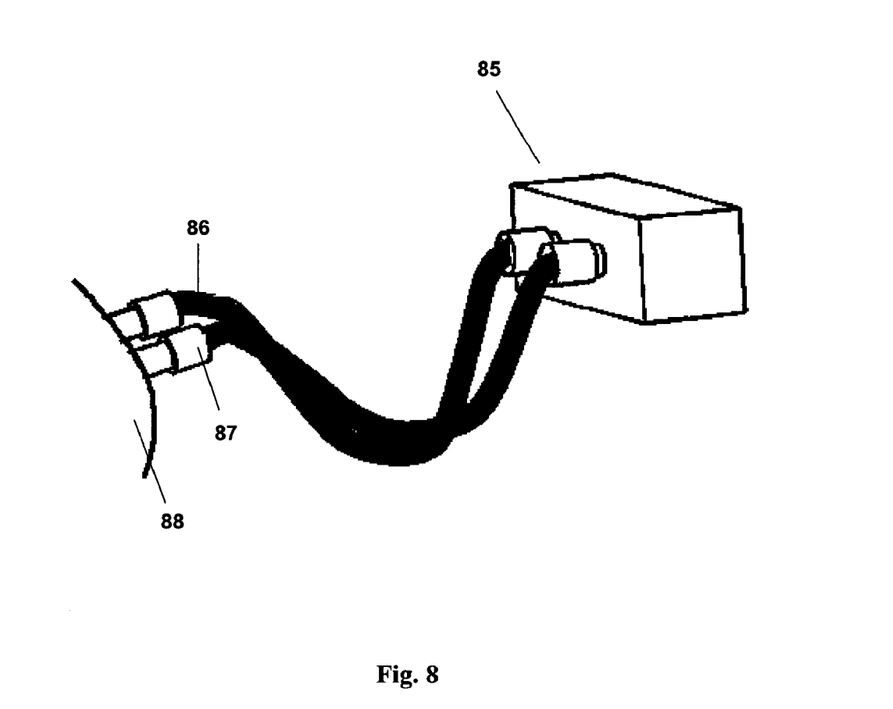
FIG. 8 is a mechanical view of a preferred embodiment.

The geometric relationship between the light delivery optics 4, the sample 5, and the detection optics 8 of the preferred photon measurement system 100 depicted in FIG. 1 is schematic and not intended to limit the possible actual physical geometry of the system. For example, the delivery optics and the detection optics may be placed on the same side of the sample 5, on opposite sides of the sample 5, or at arbitrary positions with respect to the sample 5 so long as the scattered optical wave 21 is detectable. FIG. 8 depicts a mechanical view of a preferred embodiment of the photon measurement system 100. An electronics unit 85 preferably includes the modulated optical source 3, optical detector 7, temporal response analysis engine 11, and associated electronics. Preferably the modulated optical wave 20 is delivered to the sample 5 using the delivery fiber bundle 86. The scattered optical wave 21 is delivered from the sample to the electronic unit 85 using the detection fiber bundle 87. The fiber bundles are flexible and easily repositioned with respect to the sample.

Figure 9:
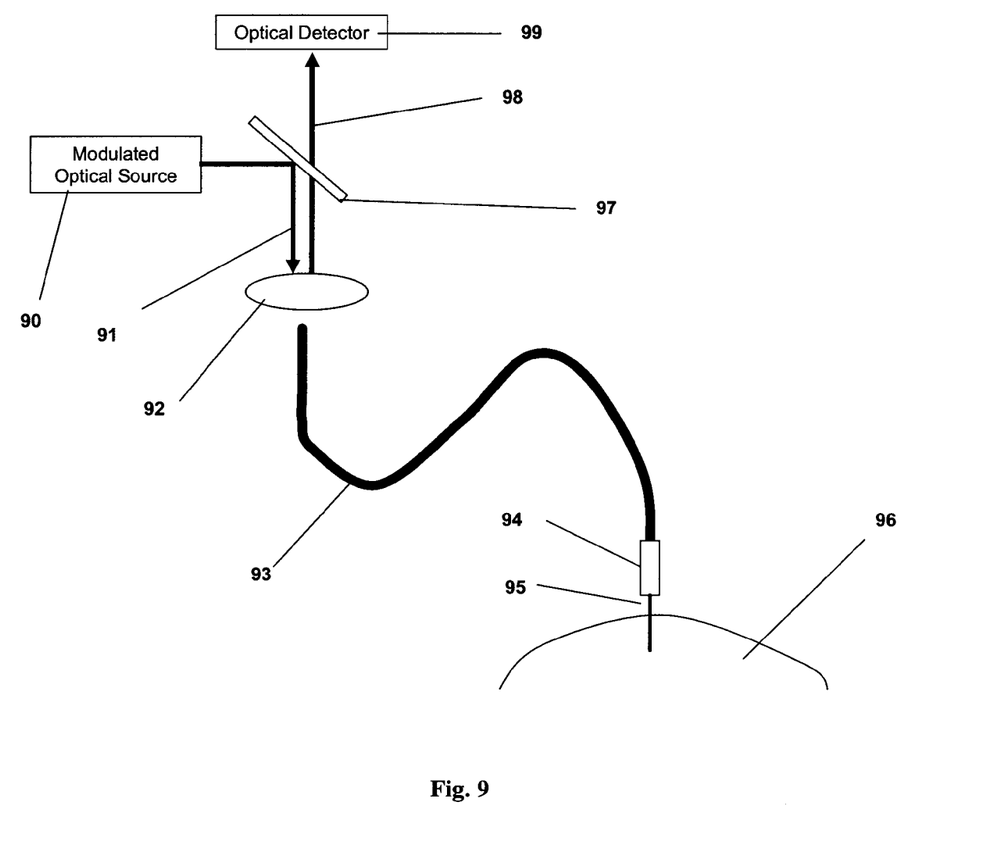
FIG. 9 is a functional representation of a preferred embodiment using a needle-based optical probe coupled to a source and a detector with a single optical fiber.
Figure 10:
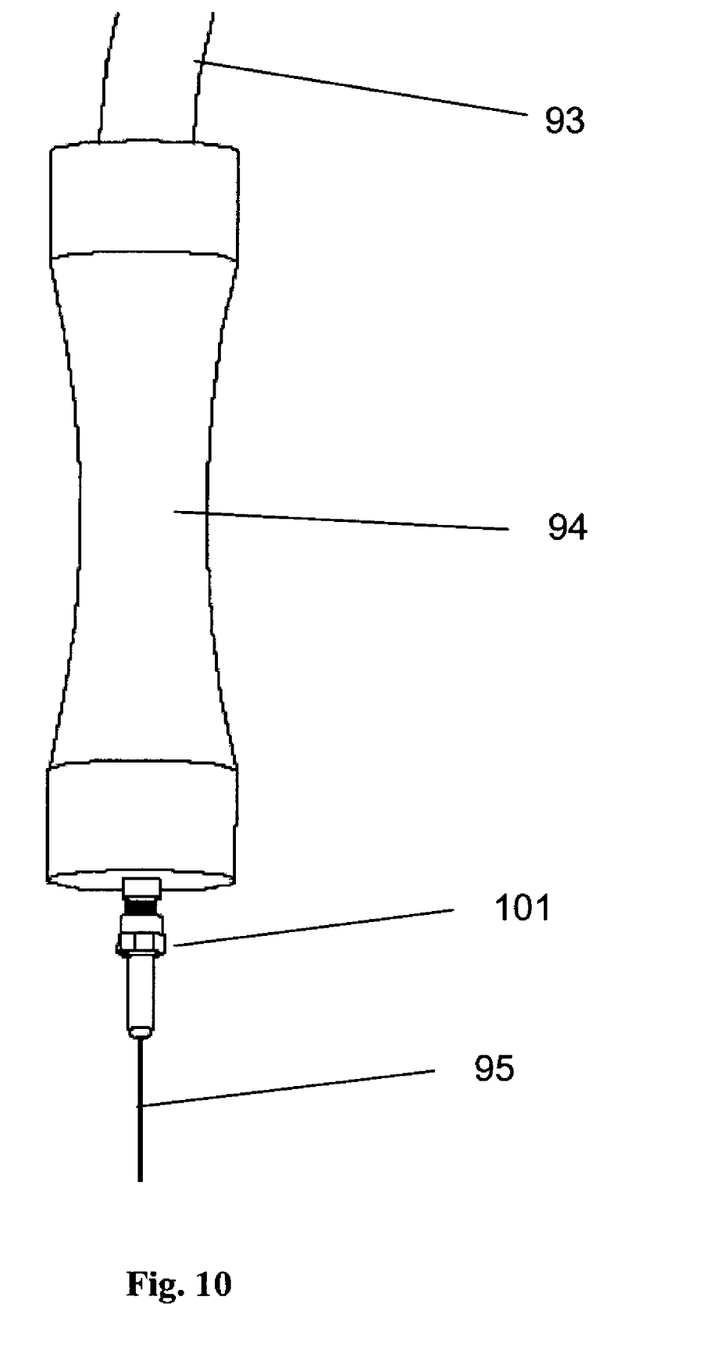
FIG. 10 depicts a preferred needle-based probe.

FIG. 9 depicts a functional representation of another preferred embodiment in which a single optical fiber serves as part of both the light delivery optics and the detection optics. The light 91 output by the modulated optical source 90 is reflected by an optical filter 97 toward coupling optics 92. The coupling optics focuses the light into an optical fiber 93 which delivers the light to an optical probe 94 with a removable needle 95. The removable needle includes a section of optical fiber allowing the light to be transmitted from the probe to the end of the needle. The needle can be inserted into a tissue sample 96 so that greater depth can be interrogated than in the case of a surface-based probe. A portion of light scattered by the tissue is coupled back into the fiber and delivered back to the coupling optics 92. A portion of this return light 98 is transmitted by the optical filter to an optical detector 99. The modulated optical source 90 and the optical detector 99 are connected to the temporal response analysis engine and associated electronics as described previously. A mechanical view of the needle-based probe is given in FIG. 10. The needle assembly 95 connects to the probe 94 with a standard SMA connector 101. In addition to the embodiments described here, other geometric arrangements of light delivery optics, detection optics, and sample are possible.

What is claimed is:

1. A cost-effective and accurate photon measurement system for human tissue comprising:
    a memory device configured to store a plurality of values corresponding to a plurality of Golay code patterns wherein said plurality of values is located by a plurality of cell addresses;
    a code selector configured to select a Golay code pattern from said plurality of Golay code patterns during operation of said photon measurement system;
    an address sequencer coupled to said memory device and said code selector configured to provide a cell address from said plurality of cell addresses corresponding to said selected Golay code pattern;
    a Golay code signal generator coupled to the code selector configured to generate a Golay code output in accordance with said selected Golay code pattern;
    a continuous wave light source coupled to the Golay code signal generator configured to generate a Golay modulated optical wave modulated in accordance with said Golay code output from the Golay code signal generator;
    delivery optics coupled to the continuous wave light source to direct the Golay modulated optical wave at a human tissue translucent material;
    an optical splitter coupled to the delivery optics between the delivery optics and the translucent material; the optical splitter coupled to an optical detector configured to direct the Golay modulated optical wave to the optical detector; the optical detector configured to generate a Golay optical reference signal; the optical detector coupled to a signal detector such that when the Golay optical reference signal is generated it is communicated to the signal detector;
    a corresponding detector configured to detect scattered optical waves from the translucent material; the corresponding detector having as an output a signal indicative of a characteristic of the detected scattered optical wave; the corresponding detector output signal communicated to the signal detector;
    the signal detector configured to generate and provide an output indicative of a characteristic of the translucent material, based in part on the Golay optical reference signal;
    a correlator coupled to the signal detector configured to generate a correlation of said signal indicative of said characteristic of the detected scattered optical wave with said Golay optical reference signal; and
    a processor coupled to said correlator configured to calculate photon time-of-flight information of said scattered optical wave based on said correlation.

2. The system of claim 1 further comprising:
    an acquisition synchronizer coupled to the corresponding detector to control acquisition of said signal indicative of said characteristic of the detected scattered optical wave; and
    a synchronization clock coupled to said acquisition synchronizer to control phase of said acquisition synchronizer and wherein the optical splitter is positioned between the continuous wave light source and the delivery optics.

3. The system of claim 1 wherein a first analog to digital converter is positioned between the optical detector and the signal detector to convert the optical reference signal into a digital signal;
    a second analog to digital converter is positioned between the corresponding detector and the signal detector to convert the corresponding detector output signal into a digital detector signal; and
    the signal detector configured to use digital processing techniques to generate the output indicative of the characteristic of the translucent material, based in part on the digitized optical reference signal.

4. The system of claim 3 wherein the signal detector comprises a detected response frame accumulator and a reference signal frame accumulator; the detected response frame accumulator having the digital detector signal as an input and the reference signal frame accumulator having the digitized optical reference signal as an input; the detected response frame accumulator configured to accumulate the digital detector signals over multiple sample times and generate an aggregated detected response signal;
    the reference signal frame accumulator configured to accumulate the digitized optical reference signals over multiple sample times and generate an aggregated reference signal;
    the reference signal frame accumulator is coupled to a plurality of programmed phase shifters such that the aggregated reference signals output from the reference signal frame accumulator form an input to the phase shifters; each phase shifter is configured to delay the aggregated reference signal a preset amount and output a delayed reference signal;
    the plurality of phase shifters are coupled to a plurality of frame correlators, number of phase shifters being equal to number of frame correlators, such that the delayed reference signal output from the phase shifter forms an input to a corresponding frame correlator;
    the detected response frame accumulator is coupled to each of the plurality of frame correlators such that the aggregated detected response signal output from the detected response frame accumulator forms an input to each of the frame correlators;
    wherein the frame correlators output a correlation signal.

5. The system of claim 1 wherein the signal detector is configured to employ temporal over-sampling to generate and provide the output indicative of the characteristic of the translucent material.

* * * * *